US010572631B2

(12) United States Patent
Nandabalan et al.

(10) Patent No.: US 10,572,631 B2
(45) Date of Patent: Feb. 25, 2020

(54) METHODS FOR REFORMULATING AND REPOSITIONING PHARMACEUTICAL DATA AND DEVICES THEREOF

(71) Applicant: BioXcel Corporation, Branford, CT (US)

(72) Inventors: Krishnan Nandabalan, Guilford, CT (US); Vimal Mehta, Guilford, CT (US); Ramkesh Meena, Bharatpur (IN)

(73) Assignee: BIOXCEL CORPORATION, Branford, CT (US)

( * ) Notice: Subject to any disclaimer, the term of this patent is extended or adjusted under 35 U.S.C. 154(b) by 295 days.

(21) Appl. No.: 15/500,802

(22) PCT Filed: Aug. 3, 2015

(86) PCT No.: PCT/US2015/043411
§ 371 (c)(1),
(2) Date: Jan. 31, 2017

(87) PCT Pub. No.: WO2016/019372
PCT Pub. Date: Feb. 4, 2016

(65) Prior Publication Data
US 2017/0220767 A1 Aug. 3, 2017

Related U.S. Application Data

(60) Provisional application No. 62/032,206, filed on Aug. 1, 2014.

(51) Int. Cl.
*G06F 7/02* (2006.01)
*G06F 16/00* (2019.01)
(Continued)

(52) U.S. Cl.
CPC .......... *G06F 19/3456* (2013.01); *G06F 16/00* (2019.01); *G06F 19/321* (2013.01);
(Continued)

(58) Field of Classification Search
CPC ...... G06F 17/30; G06F 17/30011; G06F 1/16; G06F 19/326; G06F 19/321; G06F 19/70;
(Continued)

(56) References Cited

U.S. PATENT DOCUMENTS 8,504,383 B1 * 8/2013 Malley .................... G06F 19/00
705/2
2004/0117215 A1 6/2004 Marchosky
(Continued)

FOREIGN PATENT DOCUMENTS

WO WO 2014/179513 A1 11/2014
WO WO 2016/019372 A1 2/2016
WO WO 2017/014765 A1 1/2017

OTHER PUBLICATIONS

US 7,444,292 B2, 10/2008, Marchosky (withdrawn)
(Continued)

*Primary Examiner* — Bruce M Moser
(74) *Attorney, Agent, or Firm* — Cooley LLP

(57) ABSTRACT

A method, non-transitory computer readable medium, and pharmaceutical assessment computing device that effectively reformulates and repositions pharmaceutical molecule data. With this technology, therapeutic area data comprising a medical condition and pharmaceutical molecule data corresponding to the medical condition is obtained. The pharmaceutical molecule data comprises pharmaceutical molecule identifiers and usage data parameters with corresponding usage data values for each of the pharmaceutical molecule identifiers. Each of the usage data values is compared to a corresponding usage threshold value. Reformulation opportunities are determined for each of the pharmaceutical molecule identifiers comprising a usage data value that exceeds the corresponding usage threshold value. The reformulation opportunities comprise the usage data parameters and associated usage data values corresponding
(Continued)

to the pharmaceutical molecule identifiers which comprise a usage data value that exceeds the corresponding usage threshold value. A pharmaceutical molecule report based on the reformulation opportunities is provided.

18 Claims, 4 Drawing Sheets

(51) Int. Cl.
    *G06F 19/00*     (2018.01)
    *G16C 99/00*     (2019.01)
    *G16H 10/60*     (2018.01)
    *G16B 15/00*     (2019.01)

(52) U.S. Cl.
    CPC .......... *G06F 19/326* (2013.01); *G16C 99/00* (2019.02); *G16H 10/60* (2018.01); *G16B 15/00* (2019.02)

(58) Field of Classification Search
    CPC .... G06F 19/325; G06F 19/3456; G06F 16/00; G01N 33/5008; A61K 2300/00; G16H 10/60
    See application file for complete search history.

(56) References Cited

U.S. PATENT DOCUMENTS

| | | | |
|---|---|---|---|
| 2004/0122707 A1 | 6/2004 | Sabol et al. | |
| 2005/0278185 A1 | 12/2005 | De Nijs et al. | |
| 2006/0047538 A1* | 3/2006 | Condurso | G06F 19/326 705/3 |
| 2008/0033402 A1* | 2/2008 | Blomquist | G06F 19/3456 604/890.1 |
| 2010/0198616 A1 | 8/2010 | Ghouri | |
| 2011/0246220 A1 | 10/2011 | Albert | |
| 2012/0078521 A1 | 3/2012 | Avinash et al. | |
| 2012/0078648 A1 | 3/2012 | Reiner | |
| 2012/0191469 A1 | 7/2012 | Akradi | |
| 2013/0004576 A1 | 1/2013 | Viscomi et al. | |
| 2013/0096941 A1 | 4/2013 | Kanada | |
| 2013/0096942 A1 | 4/2013 | Bowles et al. | |
| 2014/0019152 A1 | 1/2014 | Op Den Buijs et al. | |
| 2015/0039331 A1* | 2/2015 | Longman | G06F 19/326 705/2 |
| 2015/0302167 A1* | 10/2015 | Vali | G06F 19/326 705/2 |
| 2015/0338425 A1* | 11/2015 | Henske | A61K 45/06 424/9.6 |
| 2016/0063202 A1 | 3/2016 | Nandabalan et al. | |
| 2016/0246943 A1* | 8/2016 | Lake | G06F 19/3418 |

OTHER PUBLICATIONS

International Preliminary Report on Patentability, PCT appl. No. PCT/US2015/043411, 10 pages (dated Oct. 30, 2015).
International Search Report, PCT appl. No. PCT/US2015/043411, 2 pages (dated Oct. 30, 2015).
Writen Opinion of the International Searching Authority, PCT appl. No. PCT/US2015/043411, 9 pages (dated Oct. 30, 2015).
International Search Report in International Application No. PCT/US2015/041460, dated Mar. 30, 2016, 3 pages.
Written Opinion in International Application No. PCT/US2015/041460, dated Mar. 30, 2016, 6 pages.
International Preliminary Report on Patentability in International Application No. PCT/US2015/041460, dated Jan. 23, 2018, 7 pages.
International Search Report and Written Opinion in International Application No. PCT/US2014/036276 dated Sep. 25, 2014, 7 pages.
International Preliminary Report on Patentability in International Application No. PCT/US2014/036276 dated Nov. 3, 2015, 6 pages.

* cited by examiner

METHODS FOR REFORMULATING AND REPOSITIONING PHARMACEUTICAL DATA AND DEVICES THEREOF

CROSS REFERENCE TO RELATED APPLICATIONS

The present application is the U.S. national stage application of International Application No. PCT/US2015/043411, filed on Aug. 3, 2015, now International Publication No. WO 2016/019372, which claims the benefit of priority to U.S. Provisional Patent Application No. 62/032,206, filed on Aug. 1, 2014, which are hereby incorporated by reference in their entirety.

FIELD OF THE INVENTION

This technology relates to methods, computing devices, and non-transitory computer readable media for the classification, reformulation, and repositioning of pharmaceutical data.

BACKGROUND

A successful drug development process often follows a course that begins with research and development, continues with the satisfactory completion of clinical trials, and concludes with the development of a commercially viable drug product. However, a commercially viable drug product typically represents only one embodiment of the many potential drug products that may result from the pharmaceutical molecule underlying the drug product. The usefulness of a pharmaceutical molecule, both in terms of its therapeutic applications and potential for commercial benefit, is not limited to a single embodiment of the drug product. Under the right set of circumstances, the value of the drug product may be expanded through reformulation, in which a drug may be administered in different ways, such as through a different delivery mechanism, or through repositioning, in which novel uses are found for an existing drug, such as the application of the drug product to different therapeutic areas.

Existing software tools are focused on the current applications of a pharmaceutical molecule not on the potential future uses of existing pharmaceutical molecules. Further, the existing software tools represent a haphazard collection of ways to collect data, and lack a unifying framework with which to evaluate the potential ways in which pharmaceutical molecules can be reformulated or repositioned to achieve additional benefit. Additionally, existing software tools largely rely on specialized information, utilizing substantial resources during the (often times manual) data acquisition phase, and often requiring expert knowledge to analyze, organize, and interpret any information that was acquired. Given the rapid pace of drug development and the often short time frame within which the commercial potential of a pharmaceutical molecule may be realized, it is imperative that there be a way to rapidly and efficiently assess potential future uses of a pharmaceutical molecule.

Accordingly, there is a need for improved software technology that is able to determine and provide opportunities for reformulation and repositioning of a pharmaceutical molecule in a way that enhances both the therapeutic and commercial applications that can be realized from pharmaceutical molecule data. Further, there is a need for improved software technology that is able to provide reformulation opportunities and repositioning strategies in an easily navigable manner that facilitates the decision-making process with respect to a pharmaceutical molecule.

SUMMARY

A method for pharmaceutical reformulation and repositioning, comprising obtaining, by a pharmaceutical assessment computing device, therapeutic area data comprising at least one medical condition, and pharmaceutical molecule data corresponding to the at least one medical condition. The pharmaceutical molecule data comprises one or more pharmaceutical molecule identifiers and usage data parameters with corresponding usage data values for each of the one or more pharmaceutical molecule identifiers. The pharmaceutical assessment computing device compares each of the usage data values to a corresponding usage threshold value. The pharmaceutical assessment computing device determines one or more reformulation opportunities for each of the one or more pharmaceutical molecule identifiers comprising a usage data value that exceeds the corresponding usage threshold value in which the one or more reformulation opportunities comprise the usage data parameters and associated usage data values corresponding to the one or more pharmaceutical molecule identifiers comprising a usage data value that exceeds the corresponding usage threshold value. The pharmaceutical assessment computing device provides a pharmaceutical molecule report based on the one or more reformulation opportunities.

A pharmaceutical assessment computing device comprising a processor and a memory, wherein the memory is coupled to the processor which is configured to be capable of executing programmed instructions, which comprise the programmed instructions stored in the memory to: obtain therapeutic area data comprising at least one medical condition, and pharmaceutical molecule data corresponding to the at least one medical condition. The pharmaceutical molecule data comprises one or more pharmaceutical molecule identifiers and usage data parameters with corresponding usage data values for each of the one or more pharmaceutical molecule identifiers. Each of the usage data values is compared to a corresponding usage threshold value. One or more reformulation opportunities is determined for each of the one or more pharmaceutical molecule identifiers comprising a usage data value that exceeds the corresponding usage threshold value in which the one or more reformulation opportunities comprise the usage data parameters and associated usage data values corresponding to the one or more pharmaceutical molecule identifiers comprising a usage data value that exceeds the corresponding usage threshold value. A pharmaceutical molecule report based on the one or more reformulation opportunities is provided.

A non-transitory computer-readable medium having stored thereon instructions for assessing pharmaceutical data, comprising machine executable code which when executed by at least one processor, causes the processor to perform steps comprising obtaining therapeutic area data comprising at least one medical condition, and pharmaceutical molecule data corresponding to the at least one medical condition is obtained. The pharmaceutical molecule data comprises one or more pharmaceutical molecule identifiers and usage data parameters with corresponding usage data values for each of the one or more pharmaceutical molecule identifiers. Each of the usage data values is compared to a corresponding usage threshold value. One or more reformulation opportunities are determined for each of the one or more pharmaceutical molecule identifiers comprising a usage data value that exceeds the corresponding usage threshold value in which the one or more reformulation opportunities comprise the usage data parameters and associated usage data values corresponding to the one or more pharmaceutical molecule identifiers comprising a usage data value that exceeds the corresponding usage threshold value. A pharmaceutical molecule report based on the one or more reformulation opportunities is provided.

This technology offers a number of advantages including providing more effective methods, devices, and non-transitory computer readable media for pharmaceutical data reformulation and repositioning. By way of example only, with this technology, pharmaceutical molecule data for a selected therapeutic area may be analyzed to determine potential reformulation and repositioning opportunities. Further, this technology provides an efficient way to manage reformulation and repositioning activities by providing an assessment of potential opportunities in the form of a pharmaceutical molecule report, such as a reformulation or repositioning report that highlights the most favorable reformulation and repositioning opportunities. In this way, the technology may potentially forego the wasteful investment in time and resources resulting from the pursuit of less favorable reformulation and repositioning opportunities.

DETAILED DESCRIPTION

Figure 1:
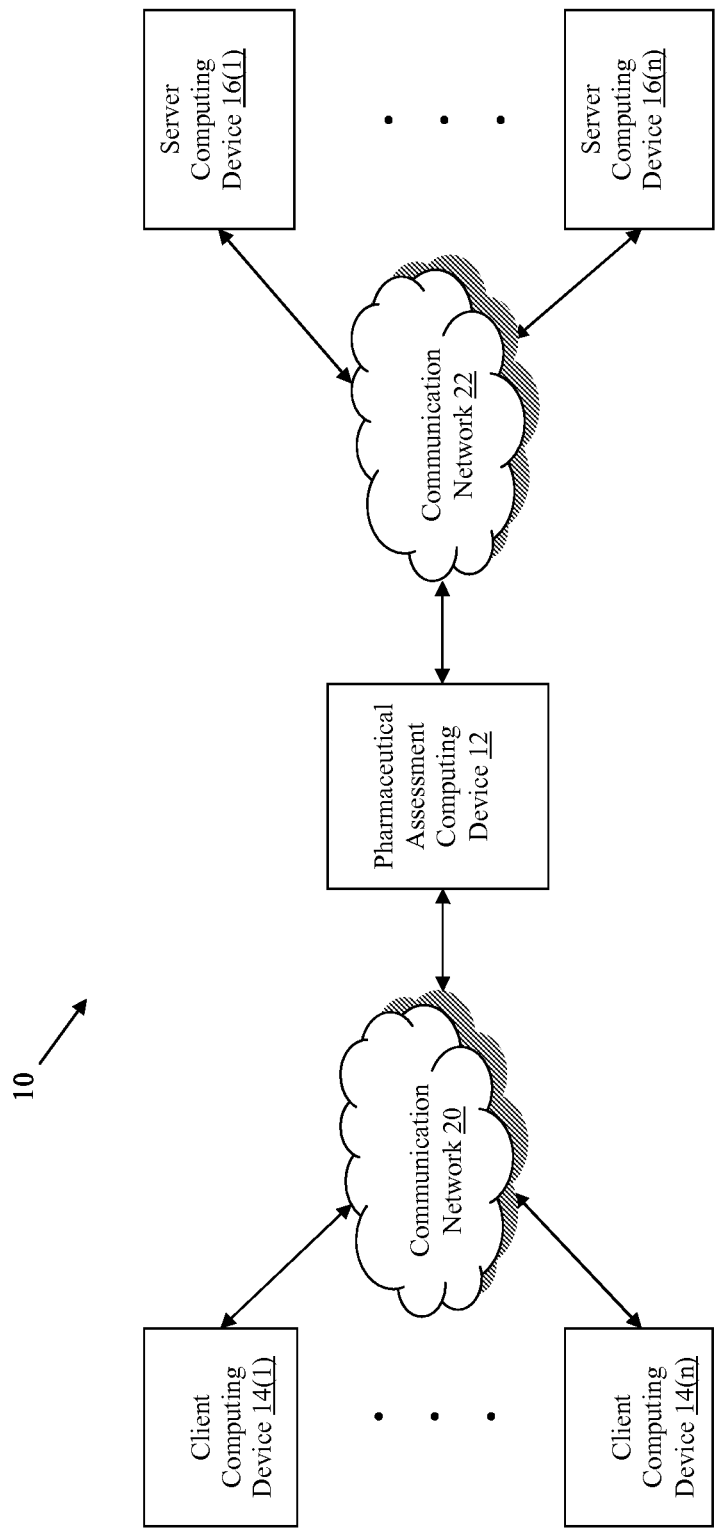
FIG. 1 is a block diagram of a network environment with an exemplary pharmaceutical assessment computing device.
Figure 2:
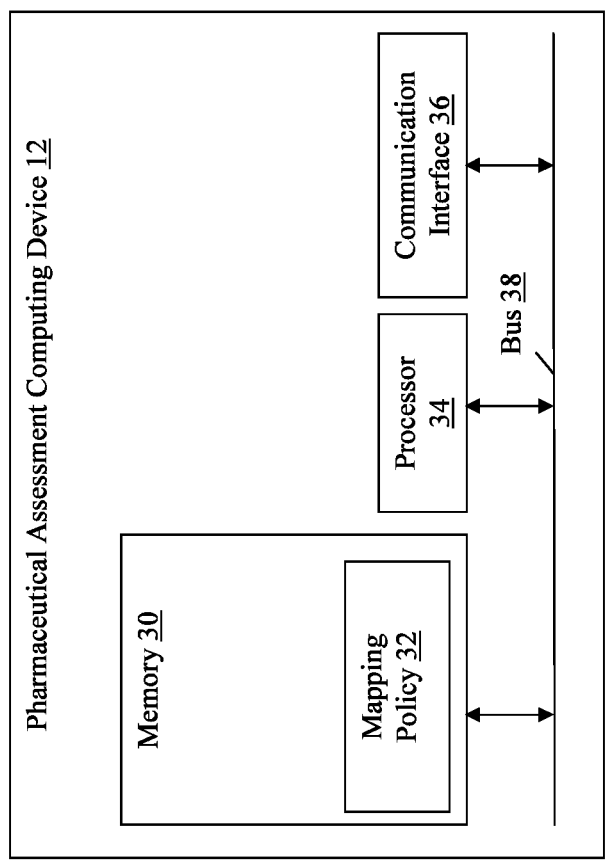
FIG. 2 is a block diagram of the exemplary pharmaceutical assessment computing device.

An example of a network environment 10 with an example of a pharmaceutical assessment computing device 12 that reformulates and repositions pharmaceutical molecule data is illustrated in FIGS. 1-2. In this particular example, the network environment 10 includes the pharmaceutical assessment computing device 12, a plurality of client computing devices 14(1)-14(n), and a plurality of server computing devices 16(1)-16(n), which are coupled together by communication network 20 and communication network 22, although the network environment 10 can include other types and/or numbers of other systems, devices, components, and/or other elements in other configurations. Further, the network environment 10 may include other network devices such as one or more routers or switches, for example, which are known to those skilled in the art and will not therefore be described here. This technology provides a number of advantages including methods, non-transitory computer readable media, and computing devices that perform assessment of pharmaceutical data.

Referring to FIGS. 1-2, the pharmaceutical assessment computing device 12 is illustrated as coupled to communication network 20, though pharmaceutical assessment computing device 12 may be coupled to other types or numbers of communication networks. The pharmaceutical assessment computing device 12 may perform any number of functions including generating usage deficit targets, providing a pharmaceutical molecule, and providing a repositioning report based on the pharmaceutical molecule data. The pharmaceutical assessment computing device 12 in this example includes a processor 34, a memory 30, and a communication interface 36 which are coupled together by one or more bus 38 or other links, although the pharmaceutical assessment computing device 12 may include other types or numbers of elements in other configurations. In this example, the bus 38 is a hyper-transport bus, although other bus types and communication links may be used, such as Peripheral Component Interconnect (PCI).

The processor 34 of the pharmaceutical assessment computing device 12 may execute one or more programmed instructions stored in the memory 30 as illustrated and described in the examples herein, although other types and numbers of functions or other operation can be performed. The processor of the pharmaceutical assessment computing device 12 may include one or more central processing units (CPUs) or general purpose processors with one or more processing cores.

The memory 30 of pharmaceutical assessment computing device 12 stores the programmed instructions and other data for one or more aspects of the present technology as described and illustrated herein, although some or all of the programmed instructions could be stored and executed elsewhere. A variety of different types of memory storage devices, such as a random access memory (RAM) or a read only memory (ROM) in the system or a floppy disk, hard disk, CD ROM, DVD ROM, or other computer readable medium which is read from and written to by a magnetic, optical, or other reading and writing system that is coupled to the processor, can be used for the memory.

In this example, the memory 30 of the pharmaceutical assessment computing device 12 includes a mapping policy 32 that may be used to map various data such as mechanism of action data and pathogenesis data. The mapping policy 32 may also be used to map pharmaceutical molecule data comprising usage data and current usage data to facilitate the provision of a pharmaceutical molecule report based on the pharmaceutical molecule data.

The communication interface 36 of the pharmaceutical assessment computing device 12 operatively couples and communicates between the pharmaceutical assessment computing device 12, client computing devices 14(1)-14(n), and server computing devices 16(1)-16(n), which are all coupled together by the communication network 20 or communication network 22, although other types and numbers of communication interfaces and connections and configurations to other equipment, systems or devices may be used.

By way of example only, the communication network 20 or communication network 22 can use Transmission Control Protocol/Internet Protocol (TCP/IP) over Ethernet and industry-standard protocols, although other types and numbers of communication networks can be used. Communication network 20 or communication network 22 in this example may employ any suitable interface mechanisms and network communication technologies including, for example, teletraffic in any suitable form (e.g., voice, modem, and the like), Public Switched Telephone Network (PSTNs), Ethernet-based Packet Data Networks (PDNs), combinations thereof, and the like.

Each of the client computing devices 14(1)-14(n) includes a processor, a memory, and a communication interface, which are coupled together by a bus or other link, although other numbers and types of network devices could be used. The client computing devices 14(1)-14(n) may run interface applications that may provide an interface to make requests for authentication, authorization, and accounting services for users, for example, via the communication network 20 and the pharmaceutical assessment computing device 12.

Each of the server computing devices 16(1)-16(n) includes a processor, a memory, and a communication interface, which are coupled together by a bus or other link, although other numbers and types of network devices could be used. The server computing devices 16(1)-16(n) may be hardware or software or may represent a system with multiple servers in a server computing device pool, which may include internal or external networks.

Although the exemplary network environment 10 with the pharmaceutical assessment computing device 12, client computing devices 14(1)-14(n), and server computing devices 16(1)-16(n), communication network 20, and communication network 22 are described and illustrated herein, other types and numbers of systems, devices, components, and elements in other topologies can be used. The systems of the examples described herein are for exemplary purposes, as many variations of the specific hardware and software used to implement the examples are possible, as will be appreciated by those skilled in the relevant art(s).

In addition, two or more computing systems or devices can be substituted for any one of the systems or devices in any example. Accordingly, principles and advantages of distributed processing, such as redundancy and replication also can be implemented, as desired, to increase the robustness and performance of the devices and systems of the examples. The examples may also be implemented on computer system(s) that extend across any suitable network using any suitable interface mechanisms and traffic technologies, including by way of example only teletraffic in any suitable form (e.g., voice and modem), wireless traffic media, wireless traffic networks, cellular traffic networks, G3 traffic networks, Public Switched Telephone Network (PSTNs), Packet Data Networks (PDNs), the Internet, intranets, and combinations thereof.

The examples may also be embodied as a non-transitory computer readable medium having instructions stored thereon for one or more aspects of the present technology as described and illustrated by way of the examples herein, which when executed by the processor, cause the processor to carry out the steps necessary to implement the methods of this technology as described and illustrated with the examples herein.

Figure 3:
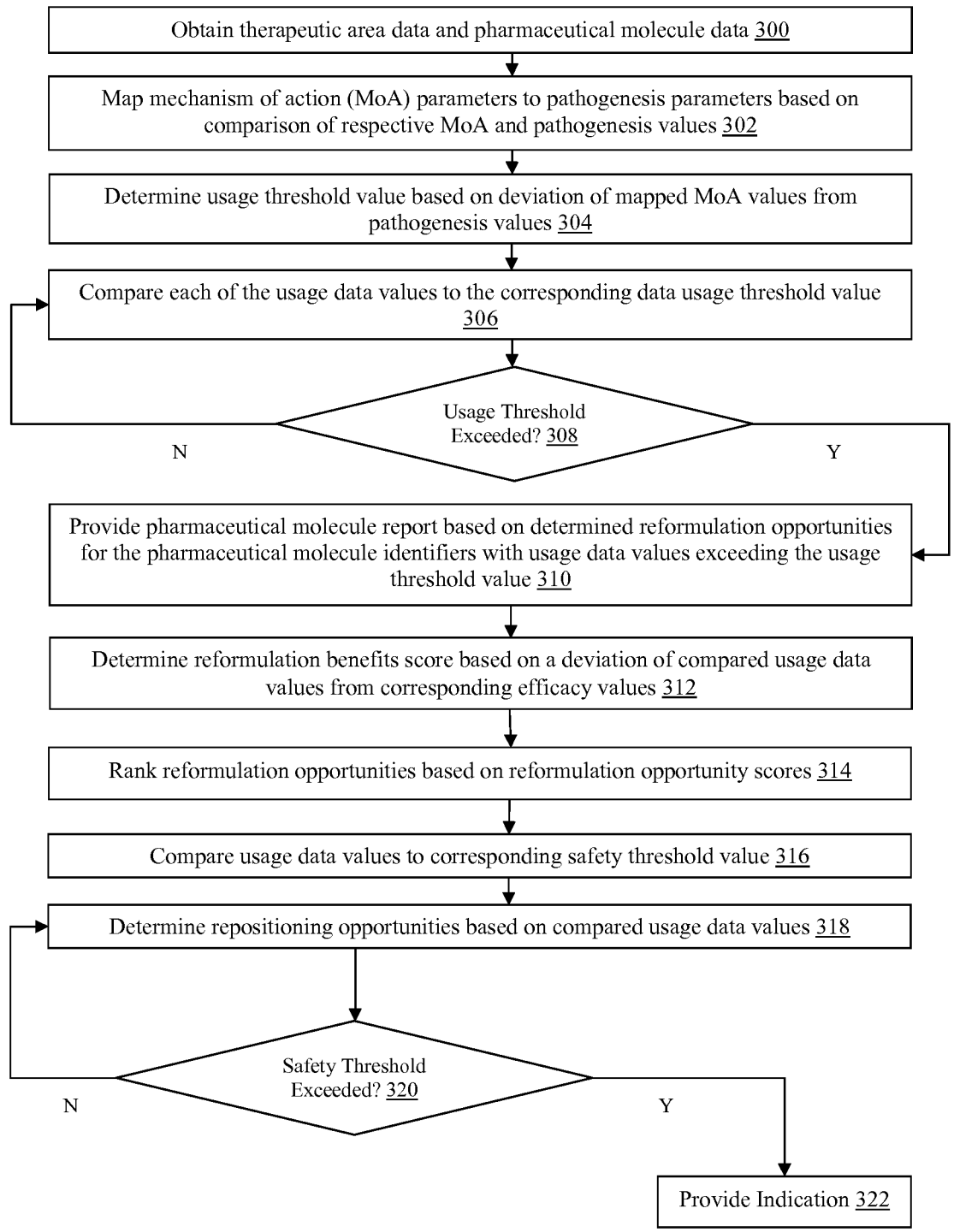
FIG. 3 is a flow chart of an example of a method for pharmaceutical molecule data reformulation and repositioning with the exemplary pharmaceutical assessment computing device.

An example of a method for assessing pharmaceutical data will now be described with reference to FIGS. 1-4. Referring more specifically to FIG. 3, an exemplary method for assessing pharmaceutical data will now be described. In step 300 in this example, a pharmaceutical assessment computing device 12 obtains therapeutic area data from server computing devices 16(1)-16(n). In an alternative example, pharmaceutical assessment computing device 12 may communicate through communication network 22 to obtain pharmaceutical data from a variety of data sources such as the United States Food and Drug Administration (FDA), European Medicines Agency (EMA), International Clinical Trials Registry Platform (ICTRP), the World Health Organization (WHO), and other repositories of medical or pharmaceutical data.

In this example, the therapeutic area data obtained from server computing devices 16(1)-16(n) comprises neurodegenerative disease data which further includes specific medical condition data comprising Multiple Sclerosis data as well as other data relating to Multiple Sclerosis such as the gender distribution, average age of onset, prevalence, incidence, and other related epidemiological data.

In an alternative example the therapeutic area may include data relating to any disease, medical condition, or therapeutic treatment area. Further, in addition to a specific therapeutic area such as Multiple Sclerosis or other diseases, the therapeutic area data may include broader categories of data relating to symptomatic data (such as for Insomnia), or general respiratory infection data which could encompass disparate therapeutic areas such as bronchitis or Cystic Fibrosis.

The pharmaceutical assessment computing device 12 also obtains pharmaceutical molecule data for the Neurodegenerative therapeutic area, from server computing devices 16(1)-16(n). In this example, the pharmaceutical molecule data includes one or more pharmaceutical molecule identifiers including Corticosteroids, Beta Interferons, Teriflumonides, Glatiramer acetates, and other pharmaceutical molecules used in the treatment of Multiple Sclerosis, though in an alternative example other pharmaceutical molecule identifiers or types of identifiers may be included in the pharmaceutical molecule data. Further the pharmaceutical molecule identifiers may include chemical formulations, trade names, or other forms of identification of the pharmaceutical molecule. Additionally, the pharmaceutical molecule data includes usage data parameters with corresponding usage data values, which may include additional data relating to the physical, chemical, and pharmacokinetic characteristics of one or more pharmaceutical molecules.

The pharmaceutical molecule identifiers include drugs that are approved for treatment of Multiple Sclerosis by a drug regulatory agency such as the United States Food and Drug Administration (FDA), European Medicines Agency (EMA), or the World Health Organization (WHO), though alternative examples include pharmaceutical molecule identifiers that are not approved by a regulatory agency or that are currently undergoing clinical testing.

In step 302, the pharmaceutical assessment computing device 12 maps different subsets of the pharmaceutical molecule data. In this example the subsets of the pharmaceutical molecule data comprise mechanism of action parameters which are mapped to corresponding pathogenesis parameters, based on a comparison of the respective mechanism of action values and pathogenesis values for each of the respective associated mechanism of action parameters and pathogenesis parameters.

The mechanism of action parameters in this example include data on the interaction between the pharmaceutical molecule and the biochemical targets, such as specific enzymes or receptors, to which the pharmaceutical molecule is targeted. In this example, the pharmaceutical molecule data for a corticosteroid compound includes data indicating the specific chemical pathway used by the corticosteroid compound as well as higher-level data such as potential side-effects and drug contraindications. Additionally, the mechanism of action parameters may include tags to associate any one of the mechanism of action parameters with a specific pharmaceutical molecule identifier which in this example is a corticosteroid compound associated with the pharmaceutical molecule identifier for that same corticosteroid compound.

The pathogenesis parameters include data describing the way in which one of the medical conditions in a therapeutic area develops over time. In this example, the pathogenesis parameters include parameters to describe the way in which Multiple Sclerosis progresses, including data on the environmental, genetic, and molecular factors that cause the disease, the progression of the disease within different age-group patients, and patient reactions to treatment including treatment with the corticosteroid compound. The pathogenesis parameters also include tags to associate any one of the pathogenesis parameters with a specific pharmaceutical molecule identifier.

By mapping subsets of the pharmaceutical data, the pharmaceutical assessment device 12 may refine or reduce the number of pharmaceutical molecule identifiers by selecting the pharmaceutical molecule identifiers based on the mapping, such as through selecting data tags in the mechanism of action parameters and pathogenesis parameters, which are associated with respective specific pharmaceutical molecule identifiers. In this way, through refinement of extraneous data in the pharmaceutical molecule data and therapeutic area data, the disclosed technology may more efficiently analyze the remaining pharmaceutical molecule data and therapeutic area data.

In an alternative example, other types of pharmaceutical molecule data or therapeutic area data may be mapped, such as: data relating to other physical, chemical, and pharmacokinetic characteristics of one or more pharmaceutical molecules; and data relating to any disease indications, epidemiological data, and other medical or pharmaceutical data related to the therapeutic area data.

In step 304, a set of usage threshold values is determined. The usage threshold values are determined on the basis of the deviation of each of the mechanism of action values associated with a mechanism of action parameter from the corresponding pathogenesis value associated with a pathogenesis parameter. In this example, the pharmaceutical identifier for the corticosteroid compound is associated with a mechanism of action parameter for the route of administration of the corticosteroid compound, which includes oral and parenteral (injection or infusion) routes of administration as well as mechanism of action values corresponding to the route of administration mechanism of action parameter, which indicate the dosages that may be administered through the respective routes of administration.

The route of administration mechanism of action values are then compared to a corresponding mapped pathogenesis value, which in this example is a pathogenesis parameter for the route of administration that may be used during various stages of Multiple Sclerosis. For example, Multiple Sclerosis may result in dysphagia which may lead to a greater deviation with mechanism of action parameters associated with an oral route of administration due to potential difficulties in swallowing a pharmaceutical molecule in a pill, or capsule form, though the deviation in this example is also balanced by oral routes of administration using a liquid form of the pharmaceutical molecule. Conversely, a parenteral route of administration mechanism of action parameter and associated value may have a lower deviation from the corresponding pathogenesis parameter and associated value, due to the avoidance of the dysphagia issues associated with an oral route of administration.

In this way, a usage threshold value is determined for each of the mapped mechanism of action and pathogenesis parameters. In this example, the usage threshold value for each mechanism of action value for the route of administration is based on a mean of the deviations of the different routes of administration and a mean of the mechanism of action values associated with the different routes of administration. However, in an alternative example, other ways of determining the usage threshold value may be used, such as a median value, or a value with outlier values removed. Additionally, in an alternative example other pharmaceutical molecule data parameters and values may be used.

In step 306, the pharmaceutical assessment computing device 12 compares each of the usage data values (determined in step 304) associated with a corresponding usage data parameter to the corresponding usage data threshold to determine whether the usage data threshold has been exceeded by the corresponding usage data value. In this example, the usage data parameters comprise the mechanism of action parameters, such as for oral or parenteral routes of administration, and the associated usage data value comprising the respective values for the different routes of administration which are based on data including clinical data indicating the relative effectiveness of each route of administration during different phases of the Multiple Sclerosis therapeutic area.

In step 308, the pharmaceutical assessment computing device 12 determines for each of the one or more pharmaceutical identifiers with which the usage data values (including the mechanism of action values) are associated, whether any one of the associated usage data values exceed the respective corresponding usage threshold value. In an alternative example, the determination may maintain a cumulative total of the number of usage data values that exceed the usage threshold value.

In step 310, the pharmaceutical assessment computing device 12 determines one or more reformulation opportunities for each pharmaceutical molecule identifier with usage data values exceeding the usage threshold value. In this way, the pharmaceutical assessment computing device 12 may more efficiently determine reformulation opportunities for each of the pharmaceutical molecule identifiers by filtering out those pharmaceutical molecule identifiers associated with usage data parameters and usage data values that are outside the range (determined by the usage threshold value) that is considered acceptable for a reformulation opportunity. In an alternative example, the reformulation opportunities may be determined for pharmaceutical molecule identifiers based on different criteria such as pharmaceutical molecule identifiers with a minimum or maximum number of usage date values that exceed the usage data threshold.

In this example, the reformulation opportunities for the pharmaceutical molecule identifier (for the corticosteroid compound) correspond with usage data parameters (each usage data parameter associated with a corresponding usage data value) and includes various routes of administration, different frequencies of administration, a specific therapeutic index, and warning and label restrictions regarding the use of the corticosteroid compound among different age groups.

Pharmaceutical assessment computing device 12 may provide the determined reformulation opportunities in the form of a pharmaceutical molecule report which includes the reformulation opportunities or other associated pharmaceutical molecule data. In an alternative example, the reformulation opportunities may include other ways in which the pharmaceutical molecule may be used in a therapeutic area context or otherwise applied to the treatment of a medical condition.

In an alternative example, other formulations or ways of delivering the pharmaceutical molecule may be included in the reformulation opportunities. Though the determination of the reformulation opportunities in this example is based on the presence of a usage data value exceeding a usage threshold value, in an alternative example, other criteria for determination of reformulation opportunities may be used.

In step 312, the pharmaceutical assessment computing device 12 determines a reformulation benefits score based on a deviation of usage data values from a corresponding efficacy values. In this example, the usage data value is a mechanism of action value for a dosage level of 10 mg twice daily of the corticosteroid compound corresponding to a dosage level parameter for a geriatric age group. The dosage level is compared to a corresponding dosage efficacy value which indicates that the recommended (in terms of efficacy) dosage level is 12 mg twice daily. Based on the deviation between the dosage level value and the dosage efficacy value, a reformulation benefits score is generated for each one of the usage data values. The reformulation benefits score reflects the extent to which the usage data values meets or exceeds a predetermined efficacy standard. The generated reformulation benefits score is added to the pharmaceutical molecule in the form of a numerical score indicating the degree to which the respective usage data value conforms to an efficacy standard.

In this example, the efficacy values are based on key opinion leader data from selected publications or governmental and non-governmental health standards, though in an alternative example the efficacy values may be based on different sources such as research for clinical or pre-clinical trials.

In step 314, in this example, the pharmaceutical assessment computing device 12 ranks the reformulation opportunities based on the reformulation benefits scores generated in step 312. In this example, the top reformulation opportunity is an increase in the frequency of administration of the corticosteroid compound to four daily doses for a geriatric population followed by various other reformulation opportunities. Further, the pharmaceutical assessment computing device 12 is able to include in the pharmaceutical molecule report, only the reformulation opportunities that exceed a predetermined threshold, though in an alternative example a different set of the ranked reformulation opportunities (including all reformulation opportunities) may be provided. The predetermined threshold may be any number of reformulation opportunities and may enhance the ease of using the disclosed technology by limiting the provision of what may in some circumstances be a very large number of reformulation opportunities. By ranking the reformulation opportunities and providing the reformulation opportunities in an accessible manner, the disclosed technology may further facilitate decision making with respect to pharmaceutical molecule data.

In step 316, the pharmaceutical assessment computing device 12 compares each of the usage data values to a corresponding threshold safety value. In this example, the usage data parameters comprise the mechanism of action parameters, such as for the recommended dosage of the corticosteroid compound, and the associated usage data value comprising the respective values of the recommended dosage for various age groups.

In step 318, of this example, the pharmaceutical assessment computing device 12 determines repositioning opportunities based on the differences between the data usage values and the threshold safety values that were compared in step 316. In this example, the repositioning opportunities are based on a repositioning framework that comprises the therapeutic area data and comprises different, potentially novel, uses of the corticosteroid compound, such as the application of the corticosteroid compound to different therapeutic areas than Multiple Sclerosis.

The pharmaceutical assessment computing device 12 determines, for each one of the pharmaceutical molecule identifiers, whether at least one of the usage data parameter values associated with the pharmaceutical molecule identifier exceeds a corresponding safety threshold value. In this example, the usage data value associated with the label restrictions indicates that the corticosteroid compound is not to be used by pregnant women and that the safety threshold value was exceeded. Though the determination of the repositioning opportunities in this example is based on whether at least one of the usage data parameter values associated with the pharmaceutical molecule identifier exceeds a corresponding safety threshold value, in an alternative example, other criteria for determination of reformulation opportunities may be used.

Accordingly, in step 320 the Yes branch is taken to step 322, since the safety threshold value was exceeded. If none of the safety threshold values were exceeded, then the No branch would be taken back to step 318 to determine further repositioning opportunities.

In step 322, the pharmaceutical assessment computing device 12 provides an indication when the usage data parameter value exceeds the corresponding safety threshold value. In this example, the indication is in the form of a written notification that the corticosteroid compound is not to be used by pregnant women, though in an alternative example, other types of indications including various audio or visual notifications may be provided.

Figure 4:
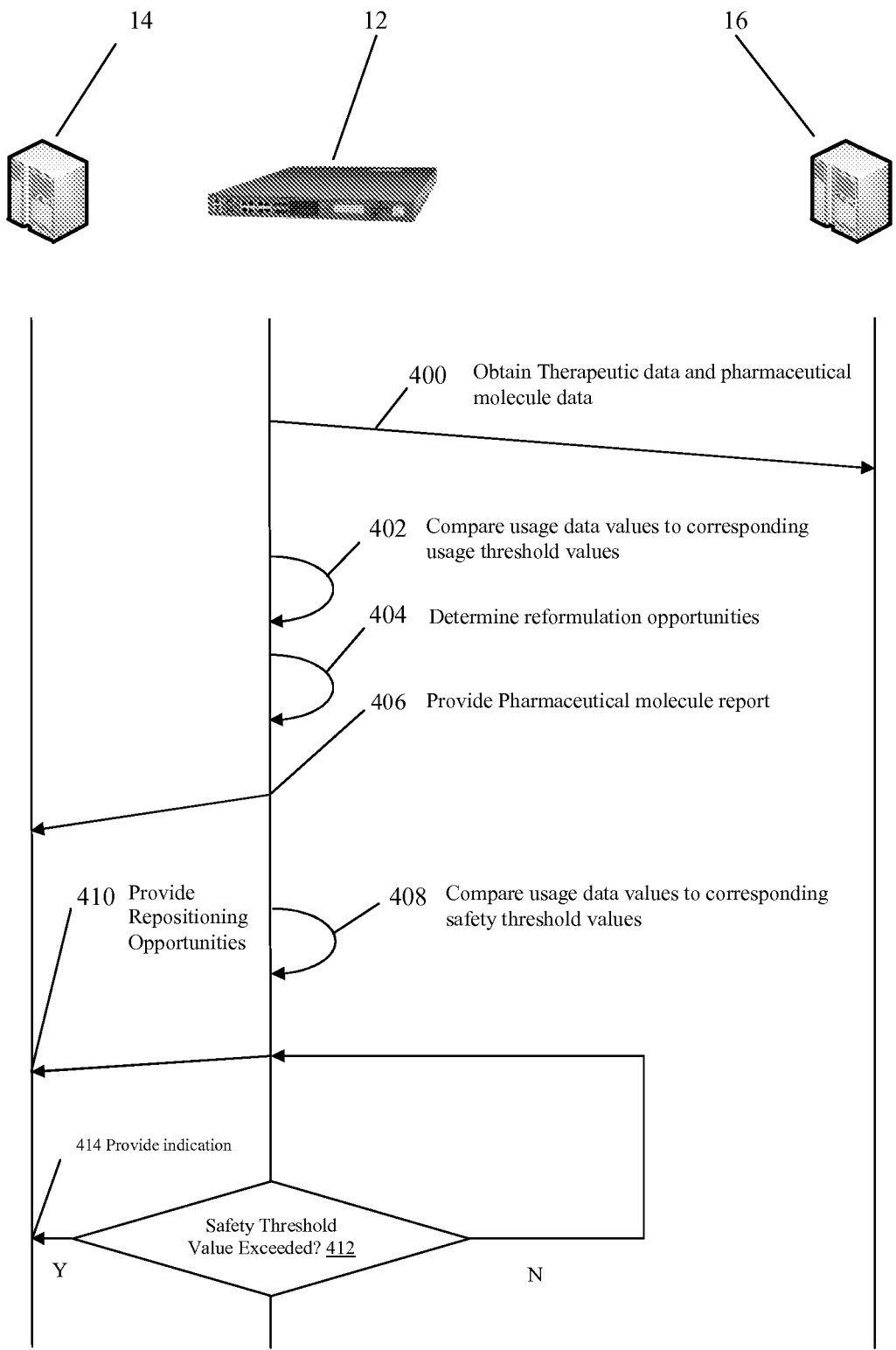
FIG. 4 is a timing diagram of an example of a method for pharmaceutical molecule data reformulation and repositioning between a pharmaceutical assessment computing device, a server computing device, and a client computing device.

Referring more specifically to FIG. 4, a timing diagram illustrating an exemplary method of reformulating and repositioning pharmaceutical molecule data is shown. In step 400 pharmaceutical assessment computing device 12 obtains therapeutic area data and pharmaceutical molecule data from server devices 16(1)-16(n), by sending one or more requests for therapeutic area data and pharmaceutical molecule data to server devices 16(1)-16(n), which responds by sending the therapeutic area data and pharmaceutical molecule data to pharmaceutical assessment computing device 12. In this example, the pharmaceutical molecule data comprises usage data parameters and corresponding usage data values, and the request is a TCP/IP (Transmission Control Protocol/Internet Protocol) request, though other communications protocols may be used.

In step 402, pharmaceutical assessment computing device 12 compares the usage data values associated with the usage parameters to corresponding usage threshold values.

In step 404, the pharmaceutical assessment computing device 12 determines one or more reformulation opportunities based on the comparison between the usage data and corresponding usage threshold data.

In step 406, the pharmaceutical assessment computing device 12 sends a pharmaceutical molecule report comprising the one or more reformulation opportunities, to the client computing devices 14(1)-14(n). In this example, the one or more reformulation opportunities comprise a set of usage data parameters and corresponding usage data values.

In step 408, the pharmaceutical assessment computing device 12 compares the usage data values associated with a usage data parameter to corresponding safety threshold values.

In step 410 pharmaceutical assessment computing device 12 provides repositioning opportunities to client computing devices 14(1)-14(n), based on the comparison of the usage data values associated with a usage data parameter to corresponding safety threshold values in step 408.

In step 412 the pharmaceutical assessment computing device 12 determines whether the safety threshold value was exceeded by the usage data value. If the safety threshold value was exceeded the Yes branch is followed to step 414 in which a notification is sent to client computing devices 14(1)-14(n) to indicate that the safety threshold value was exceeded by the usage data value. If the safety threshold value was not exceeded, the No branch is taken to step 410 in which further repositioning opportunities are provided to client computing devices 14(1)-14(n).

Accordingly, as illustrated and described by way of the examples herein, this technology provides effective methods, a non-transitory computer readable medium, and devices for reformulation and repositioning of pharmaceutical molecule data. With this technology, therapeutic area data and pharmaceutical molecule data are obtained, and reformulation or repositioning opportunities are provided based on the obtained pharmaceutical molecule data and therapeutic area data. Further, the disclosed technology also compares reformulation opportunities in order to provide a ranking of the relative value of the respective reformulation opportunities. Additionally, by mapping current usage data to pharmaceutical molecule identifiers, the disclosed technology is able to provide one or more repositioning opportunities so that the pharmaceutical molecule can be used to treat different medical conditions.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Additionally, the recited order of processing elements or sequences, or the use of numbers, letters, or other designations therefore, is not intended to limit the claimed processes to any order except as may be specified in the claims. Accordingly, the invention is limited only by the following claims and equivalents thereto.

What is claimed is:

1. A method for pharmaceutical reformulation of a drug, the method comprising:

obtaining, by a pharmaceutical assessment computing device, (1) therapeutic area data comprising at least one medical condition, pathogenesis parameters and associated pathogenesis values, and (2) pharmaceutical molecule data corresponding to the at least one medical condition, wherein the pharmaceutical molecule data comprises a set of pharmaceutical molecule identifiers, and mechanism of action parameters and associated mechanism of action values for each pharmaceutical molecule identifier of the set of pharmaceutical molecule identifiers;

refining, by the pharmaceutical assessment computing device, a number of pharmaceutical molecule identifiers for analysis by the pharmaceutical assessment computing device to define a subset of pharmaceutical molecule identifiers from the set of pharmaceutical molecule identifiers by mapping the mechanism of action parameters to the pathogenesis parameters using the associated pathogenesis values and the associated mechanism of action values and selecting tags associated with the mechanism of action parameters and tags associated with the pathogenesis parameters to define usage data parameters including mapped mechanism of action parameters and usage data values including mapped mechanism of action values;

comparing, by the pharmaceutical assessment computing device, each of the usage data values to a corresponding usage threshold value;

determining, by the pharmaceutical assessment computing device, one or more different delivery mechanisms for each pharmaceutical molecule identifier from the subset of pharmaceutical molecule identifiers comprising a usage data value that exceeds the corresponding usage threshold value, the one or more different delivery mechanisms being associated with the usage data parameters and associated usage data values corresponding to the pharmaceutical molecule identifiers from the subset of pharmaceutical molecule identifiers comprising a usage data value that exceeds the corresponding usage threshold value; and providing, by the pharmaceutical assessment computing device, a pharmaceutical molecule report based on the one or more different delivery mechanisms.

2. The method according to claim 1, further comprising:
determining, by the pharmaceutical assessment computing device, a deviation of each mechanism of action value associated with a mapped mechanism of action parameter from the pathogenesis value associated with a corresponding mapped pathogenesis parameter, wherein the usage threshold value is based on the determined deviation.

3. The method according to claim 1, further comprising:
comparing, by the pharmaceutical assessment computing device, the usage data values associated with a corresponding usage data parameter to a corresponding efficacy value associated with an efficacy parameter corresponding to the usage data parameter; and generating, by the pharmaceutical assessment computing device, a reformulation benefits score based on deviations of each of the compared usage data values from the corresponding efficacy values, wherein the pharmaceutical molecule report further comprises the generated reformulation benefits score.

4. The method according to claim 3, further comprising:
ranking, by the pharmaceutical assessment computing device, the one or more different delivery mechanisms based on the generated reformulation benefits score for each of the one or more different delivery mechanisms, wherein only the one or more different delivery mechanisms ranked higher than a predetermined ranking threshold are included in the pharmaceutical molecule report.

5. The method according to claim 1, further comprising:
comparing, by the pharmaceutical assessment computing device, each of the usage data values associated with a corresponding pharmaceutical molecule identifier from the set of pharmaceutical molecule identifiers to a corresponding safety threshold value; and determining, by the pharmaceutical assessment computing device, one or more repositioning opportunities for each of the pharmaceutical molecule identifiers that comprise only usage data values that exceed the corresponding safety threshold value, wherein the one or more repositioning opportunities are based on a repositioning framework comprising the therapeutic area data and the pharmaceutical molecule report is further based on the one or more repositioning opportunities.

6. The method according to claim 5, further comprising:
providing, by the pharmaceutical assessment computing device, an indication for each pharmaceutical molecule identifier from the set of pharmaceutical molecule identifiers that comprises at least one usage data value that does not exceed the corresponding safety threshold value.

7. A pharmaceutical assessment computing device, comprising:
- at least one processor; and
- a memory, wherein the memory is coupled to the at least one processor which is configured to be capable of executing programmed instructions, which comprise the programmed instructions stored in the memory to:
  - obtain (1) therapeutic area data comprising at least one medical condition, pathogenesis parameters and associated pathogenesis values, and (2) pharmaceutical molecule data corresponding to the at least one medical condition, wherein the pharmaceutical molecule data comprises a set of pharmaceutical molecule identifiers, and mechanism of action parameters and associated mechanism of action values for each pharmaceutical molecule identifier of the set of pharmaceutical molecule identifiers;
  - refine a number of pharmaceutical molecule identifiers for analysis by the at least one processor to define a subset of pharmaceutical molecule identifiers from the set of pharmaceutical molecule identifiers by mapping the mechanism of action parameters to the pathogenesis parameters using the associated pathogenesis values and the associated mechanism of action values and selecting tags associated with the mechanism of action parameters and tags associated with the pathogenesis parameters to define usage data parameters including mapped mechanism of action parameters and usage data values including mapped mechanism of action values;
  - compare each of the usage data values to a corresponding usage threshold value;
  - determine, one or more different delivery mechanisms for each pharmaceutical molecule identifier from the subset of pharmaceutical molecule identifiers comprising a usage data value that exceeds the corresponding usage threshold value, the one or more different delivery mechanisms being associated with the usage data parameters and associated usage data values corresponding to the pharmaceutical molecule identifiers from the subset of pharmaceutical molecule identifiers comprising a usage data value that exceeds the corresponding usage threshold value; and
  - provide a pharmaceutical molecule report based on the one or more different delivery mechanisms.

8. The device according to claim 7, wherein the processor is further configured to be capable of executing programmed instructions, which comprise programmed instructions stored in the memory to:
- generate a deviation of each mechanism of action value associated with a mapped mechanism of action parameter from the pathogenesis value associated with a corresponding mapped pathogenesis parameter, wherein the usage threshold value is based on the generated deviation.

9. The device according to claim 7, wherein the processor is further configured to be capable of executing programmed instructions, which comprise programmed instructions stored in the memory to:
- compare the usage data values associated with a corresponding usage data parameter to a corresponding efficacy value associated with an efficacy parameter corresponding to the usage data parameter; and
- generate a reformulation benefits score based on deviations of each of the compared usage data values from the corresponding efficacy values, wherein the pharmaceutical molecule report further comprises the generated reformulation benefits score.

10. The device according to claim 9, wherein the processor is further configured to be capable of executing programmed instructions, which comprise programmed instructions stored in the memory to:
- rank the one or more different delivery mechanisms based on the generated reformulation benefits score for each of the one or more different delivery mechanisms, wherein the pharmaceutical molecule report further comprises the determined reformulation benefits score.

11. The device according to claim 7, wherein the processor is further configured to be capable of executing programmed instructions, which comprise programmed instructions stored in the memory to:
- compare each of the usage data values associated with a corresponding pharmaceutical molecule identifier from the set of pharmaceutical molecule identifiers to a corresponding safety threshold value; and
- determine one or more repositioning opportunities for each of the pharmaceutical molecule identifiers that comprise only usage data values that exceed the corresponding safety threshold value, wherein the one or more repositioning opportunities are based on a repositioning framework comprising the therapeutic area data and the pharmaceutical molecule report is further based on the one or more repositioning opportunities.

12. The device according to claim 11, wherein the processor is further configured to be capable of executing programmed instructions, which comprise programmed instructions stored in the memory to:
- provide an indication for each pharmaceutical molecule identifier from the set of pharmaceutical molecule identifiers that comprises at least one usage data value that does not exceed the corresponding safety threshold value.

13. A non-transitory computer readable medium having stored thereon instructions for assessing pharmaceutical data, comprising machine executable code which when executed by at least one processor, causes the at least one processor to perform steps comprising:
- obtaining (1) therapeutic area data comprising at least one medical condition, pathogenesis parameters and associated pathogenesis values, and (2) pharmaceutical molecule data corresponding to the at least one medical condition, wherein the pharmaceutical molecule data comprises a set of pharmaceutical molecule identifiers, and mechanism of action parameters and associated mechanism of action values for each pharmaceutical molecule identifier of the set of pharmaceutical molecule identifiers;
- refining a number of pharmaceutical molecule identifiers for analysis by the at least one processor to define a subset of pharmaceutical molecule identifiers from the set of pharmaceutical molecule identifiers by mapping the mechanism of action parameters to the pathogenesis parameters using the associated pathogenesis values and the associated mechanism of action values and selecting tags associated with the mechanism of action parameters and tags associated with the pathogenesis parameters to define usage data parameters including mapped mechanism of action parameters and usage data values including mapped mechanism of action values;
- comparing each of the usage data values to a corresponding usage threshold value;

determining, one or more different delivery mechanisms for each pharmaceutical molecule identifier from the subset of pharmaceutical molecule identifiers comprising a usage data value that exceeds the corresponding usage threshold value, the one or more different delivery mechanisms being associated with the usage data parameters and associated usage data values corresponding to the pharmaceutical molecule identifiers from the subset of pharmaceutical molecule identifiers comprising a usage data value that exceeds the corresponding usage threshold value; and providing a pharmaceutical molecule report based on the one or more different delivery mechanisms.

14. The medium according to claim 13, further having stored thereon instructions that when executed by the at least one processor cause the at least one processor to perform steps further comprising:

determining a deviation of each mechanism of action value associated with a mapped mechanism of action parameter from the pathogenesis value associated with a corresponding mapped pathogenesis parameter, wherein the usage threshold value is based on the determined deviation.

15. The medium according to claim 13, further having stored thereon instructions that when executed by the at least one processor cause the at least one processor to perform steps further comprising:

comparing the usage data values associated with a corresponding usage data parameter to a corresponding efficacy value associated with an efficacy parameter corresponding to the usage data parameter; and generating a reformulation benefits score based on deviations of each of the compared usage data values from the corresponding efficacy values, wherein the pharmaceutical molecule report further comprises the generated reformulation benefits score.

16. The medium according to claim 15, further having stored thereon instructions that when executed by the at least one processor cause the at least one processor to perform steps further comprising:

ranking the one or more different delivery mechanisms based on the generated reformulation benefits score for each of the one or more different delivery mechanisms, wherein only the one or more different delivery mechanisms ranked higher than a predetermined ranking threshold are included in the pharmaceutical molecule report.

17. The medium according to claim 13, further having stored thereon instructions that when executed by the at least one processor cause the at least one processor to perform steps further comprising:

comparing each of the usage data values associated with a corresponding pharmaceutical molecule identifier from the set of pharmaceutical molecule identifiers to a corresponding safety threshold value; and determining one or more repositioning opportunities for each of the pharmaceutical molecule identifiers that comprise only usage data values that exceed the corresponding safety threshold value, wherein the one or more repositioning opportunities are based on a repositioning framework comprising the therapeutic area data and the pharmaceutical molecule report is further based on the one or more repositioning opportunities.

18. The medium according to claim 17, further having stored thereon instructions that when executed by the at least one processor cause the at least one processor to perform steps further comprising:

providing an indication for each pharmaceutical molecule identifier from the set of pharmaceutical molecule identifiers that comprises at least one usage data value that does not exceed the corresponding safety threshold value.

* * * * *